(12) United States Patent
Martini

(10) Patent No.: US 6,558,392 B1
(45) Date of Patent: May 6, 2003

(54) LOCK REDUCTION DEVICE AND METHOD

(76) Inventor: Giuseppe Martini, Viale Mazzini, 134-00195 Rome (IT)

( * ) Notice: Subject to any disclaimer, the term of this patent is extended or adjusted under 35 U.S.C. 154(b) by 192 days.

(21) Appl. No.: 09/724,189

(22) Filed: Nov. 28, 2000

Related U.S. Application Data

(63) Continuation-in-part of application No. 09/312,521, filed on May 14, 1999, now Pat. No. 6,168,601.

(51) Int. Cl.[7] .............................. A61F 2/00; A61B 1/32
(52) U.S. Cl. ......................... 606/90; 606/208; 600/239; 433/140
(58) Field of Search .......................... 606/90, 205–208; 600/237–239, 243, 244; 433/140

(56) References Cited

U.S. PATENT DOCUMENTS

| 390,561 | A | * | 10/1888 | Brown ........................ 24/267 |
| 485,609 | A | * | 11/1892 | Casebeer ..................... 433/93 |
| 888,484 | A | * | 5/1908 | Gehorsam ................... 43/53.5 |
| 1,918,889 | A | * | 7/1933 | Bacon ........................ 251/9 |
| 2,075,534 | A | * | 3/1937 | McCormack ............... 600/219 |
| 4,955,367 | A | * | 9/1990 | Homsy ....................... 433/215 |
| 5,050,586 | A | * | 9/1991 | Bonnell ...................... 433/42 |
| 5,312,420 | A | * | 5/1994 | Toso et al. .................. 606/138 |
| 5,484,447 | A | * | 1/1996 | Waldock et al. ............. 33/511 |
| 5,810,586 | A | * | 9/1998 | Fjelstad ...................... 33/513 |
| 6,168,601 | B1 | * | 1/2001 | Martini ....................... 433/140 |

* cited by examiner

Primary Examiner—Michael Peffley
(74) Attorney, Agent, or Firm—Foley & Lardner

(57) ABSTRACT

A device and method for distracting a temporomandibular joint and/or repositioning a dislocated disc in a patient. The device comprises upper and lower elongated members that are releasably coupled together by an arrangement that allows pivoting and sliding relative movement. Each member includes a handle at one end and an opposite distal tip configured for engaging teeth of the upper and lower jaws. The lower member includes a clamp for adjustably securing the patient's mandible to the lower member. The device may also include an auxiliary, height adjustable fulcrum located forwardly of the coupling between the members. The auxiliary fulcrum permits the operator to obtain a more advantageous lever, which is useful for freeing a locked jaw in a patient suffering from intra-articular adhesions. The distal tips and/or receptacles mounted on the distal tips may be detachable from a base portion of the device to enhance adaptability of the device to different size patients and anatomies. The receptacles may be pre-filled with impression material and/or disposable. The method of using the device includes positioning the device in the patient's mouth so that the distal tips engage teeth in the upper and lower half-arches of the patient, and squeezing the first and second handles together to separate the distal tips and distract the temporomandibular joint. The lower member may then be slid longitudinally relative to the upper member to reestablishing a normal or improved condyle-disc relationship.

33 Claims, 7 Drawing Sheets

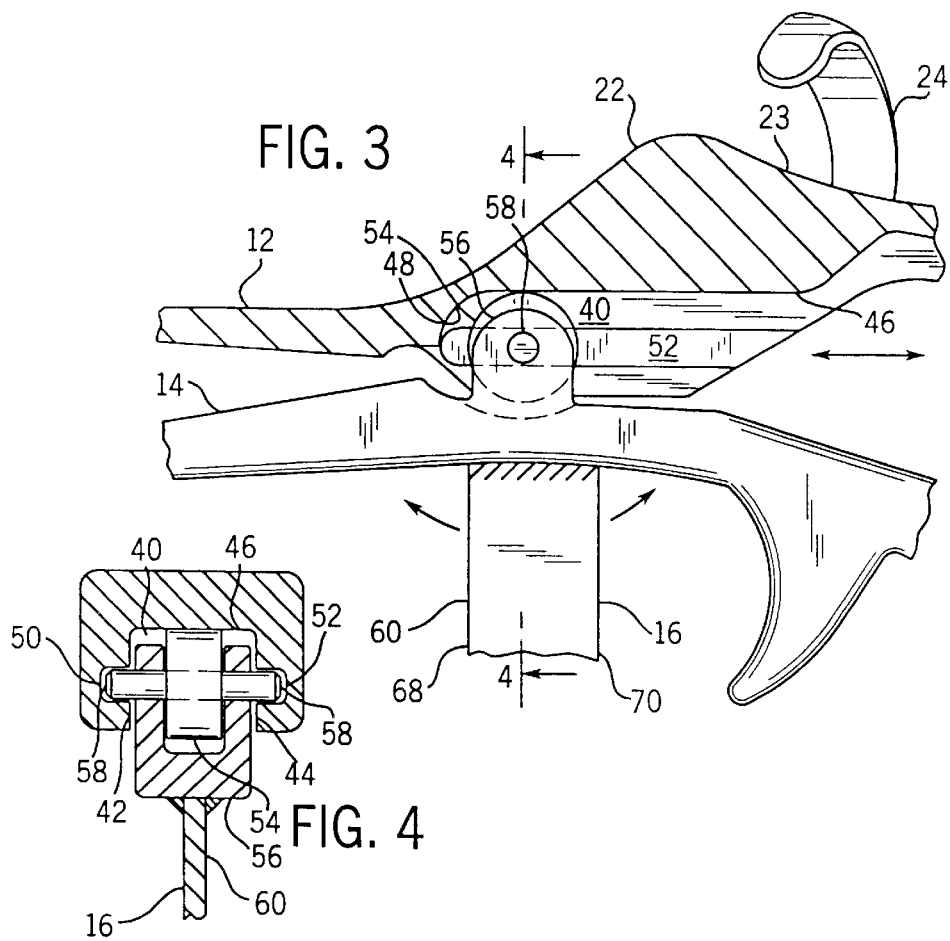
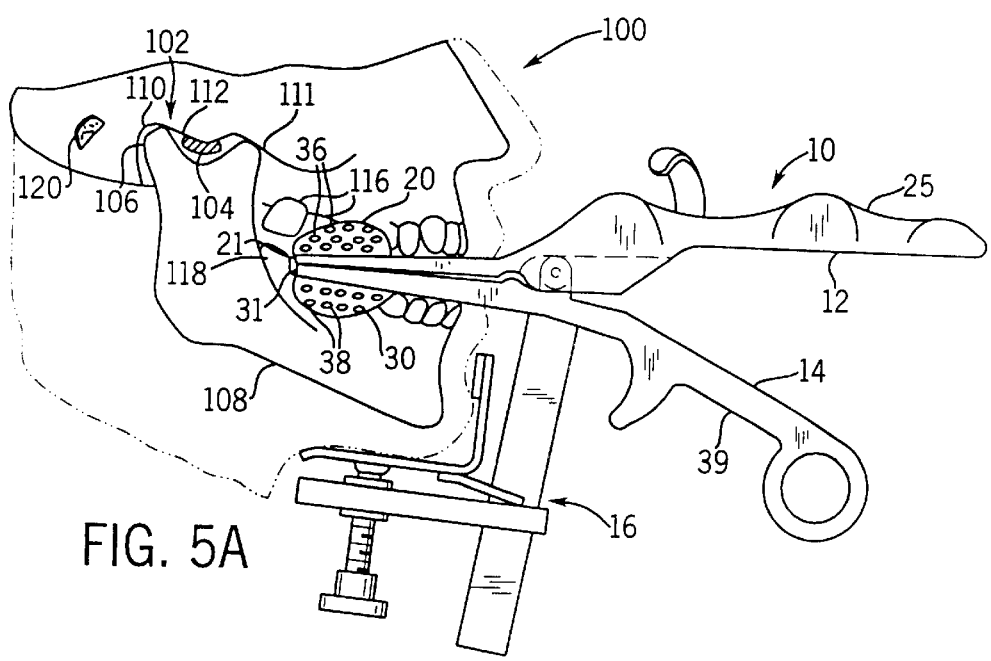

LOCK REDUCTION DEVICE AND METHOD

RELATED APPLICATIONS

This application is a continuation-in-part of U.S. Ser. No. 09/312,521, filed May 14, 1999, now U.S. Pat. No. 6,168,601.

FIELD OF THE INVENTION

The present invention relates to mechanical devices for manipulating temporomandibular joints and, more particularly, to devices for reducing or repairing dysfunctional disturbances of the masticatory system. Specifically, this invention relates to a device and method for reestablishing a normal or improved condyle-disc relationship in patients with a dislocated disc. The invention also includes a device and method for distracting the temporomandibular joint in patients suffering from intra-articular adhesions.

BACKGROUND OF THE INVENTION

The temporomandibular joint is a compound multiaxial joint constructed to permit different types of movement (hinge and glide articulation) of the mandible and different degrees of mouth opening. This is made possible by the presence of an articular disc (or meniscus) interposed between the condyle of the mandible and the glenoid (or mandibular) fossa of the temporal bone. The articular disc divides the joint into an upper (glenoid fossa-disc) and a lower (condyle-disc) compartment. In the normal relation, the condyle sits in the articular fossa with its anterior-superior surface closely approximating the posterior-inferior surface of the articular eminence of the temporal bone. A thin portion of the disc rests between the two surfaces, and a thickened portion of the disc rests at the superior angle of the condyle.

Normally, when the jaws are closed, the condyle contacts the disc and the disc contacts the glenoid fossa. If contact is maintained between the upper and lower teeth while gliding movements are performed, this contact relationship should be maintained. During opening movements, a smooth gliding relationship between the upper and lower compartments of the joint should also be maintained. The first phase in mouth opening is a simple hinge action, which involves only the lower (condyle-disc) compartment of the joint. Specifically, it consists of the condyle head rotating around a point on the under surface of the disc, while the body of the mandible drops almost passively downward and backward.

The second phase in mouth opening involves the lower and upper compartments of the joint and consists of a gliding of the condyle and disc forward and downward along the articular eminence. This occurs alone during protrusion and lateral movements of the mandible and in combination with the hinge action during the wider opening of the mouth. A wide opening of the mouth would be impossible with a simple hinge movement since the posterior surface of the ramus would compress the soft tissue between the mandible and the mastoid process. The gliding action brings the ramus forward and also downward so that the hinge action can continue.

Several types of temporomandibular joint dysfunctions can reduce or prevent a wide opening of the mouth. One common joint dysfunction is known as an anteriorly dislocated disc—also known as a posterior condylar displacement. In the temporomandibular joint, the space posterior to the condyle is filled with fibrous tissue that is compressible. The posterior attachment of the superior head of the external pterygoid muscle is posterior on the neck of the condyle. This attachment can stretch or "break down" along with the tight lateral and medial fibers attaching disc and condyle, thus allowing the disc to slide anteriorly on the condyle. If the disc slides anteriorly to the point that the thick portion of the disc rests on the anterior-superior surface of the condyle—instead of its normal resting position on the superior angle of the condyle—this condition is known as a complete anterior dislocation of the disc or a lodged disc.

In patients with a complete anterior dislocation of the disc, the range of condylar translation is limited by the anteriorly dislocated disc on the affected side. This condition often progresses from intermittent locking to acute locking, which usually becomes permanent. A lodged disc forces the condyle to "slip or snap" over the thickened portion of the disc, which may thicken even further as the condition becomes more chronic due to folding of the disc. Thus, the patient experiences a "click" as the teeth are occluded because the condyle is displaced posteriorly but the disc is not, and another "click" occurs as the patient's mouth is opened and the structures regain their normal relations.

A known technique for reducing an anteriorly dislocated disc involves manually manipulating the jaw in an effort to assist the patient to unlock his or her jaw. This is accomplished by an operator or clinician simultaneously pushing down on the lower posterior teeth (or half-arch) while pulling up on the patient's chin. This maneuver is designed to distract the joint. During the first part of the maneuver the mandible must be kept in a retruded (or rearward) position. Importantly, the mandible must never be forcibly pulled forward or forcibly opened unless the joint is also being distracted, as this could damage the joint.

Keeping the mandible in a retruded position, the operator continues to press downward on the posterior teeth (or half-arch) and pull up on the chin. After a few moments, the patient is instructed to move the jaw from side to side, concentrating on moving it toward the side opposite the dislocated disc. While the joint is being distracted and the operator and patient are moving the jaw to the opposite side, the disc will hopefully snap back into place. Although this can sometimes be felt or heard, in some instances there is no noise or other physical evidence that the disc has been repositioned other than the return of full range of lateral movement to the opposite side of the jaw.

After the dislocated joint has been reduced (or the range of movement to the opposite side increased), the patient is instructed to not close the teeth together until a mouth prop can be inserted, which will maintain the mandible in an open position. After keeping the mandible in the open position for about fifteen minutes, the mouth prop is removed and replaced with a repositioning splint (or bite plane). This splint is prepared ahead of time and typically has an extremely large flange extending downward anteriorly to engage the lingual surfaces of the lower cuspids, bicuspids, and incisors so that the patient cannot retrude the mandible when it is near the closed jaw position. The splint will typically maintain the mandible forward of its previous intercuspal position by about 3 mm to 5 mm. The splint remains in place for twenty-four hours a day for at least two weeks, except for brief occasions when the splint is removed for cleaning and brushing of the teeth, during which the mouth prop is used to maintain the jaw in the open position. This period of at least two weeks during which the patient's jaw is maintained in the open position gives the disc a chance to heal.

Another common temporomandibular joint dysfunction that can reduce or prevent a wide opening of the mouth is intra-articular adhesions. Intraarticular adhesions involve an abnormal union of separate tissue surfaces by new fibrous tissue resulting from an inflammatory process. In the temporomandibular joint, the newly formed uniting tissue may form between the anterior-superior surface of the articular fossa and the posterior-inferior surface of the articular eminence of the temporal bone. In patients suffering from such intra-articular adhesions, the temporomandibular joint becomes significantly more difficult to distract due to the increased force that must be applied to overcome the adhesions.

The present invention provides a device that facilitates the operator in distracting the temporomandibular joint and reestablishing the proper condyle-discfossa relationship. The invention also provides a device that is readily adapted to allow increased leverage by the operator when necessary to free the jaw from intraarticular adhesions or other abnormal locking conditions. The device is also advantageous in that permits the operator to more accurately control both the direction and magnitude of forces applied to the patient's mandible than is possible by hand manipulations alone. Another marked advantage of the device is it substantially reduces the risk of the mandible being forcibly pulled forward or forcibly opened unless the joint is also being distracted.

SUMMARY OF THE INVENTION

This invention provides a device for distracting a temporomandibular joint in a patient. The device comprises first and second elongated members movably coupled together. Each member includes a handle at one end and an opposite distal tip configured for engaging teeth of the upper or lower jaws. In a preferred form of the invention, the movable coupling is a pivotable, slidable, and releasable coupling. In another preferred form of the invention, the second member includes a clamp for adjustably securing the patient's mandible to the second member.

The invention also provides a device for repositioning a dislocated disc in a temporomandibular joint of a patient. The device comprises upper and lower members movably coupled together. The upper member includes a handle at one end and an upwardly facing surface at an opposite end configured for engaging posterior teeth (or the entire half-arch) of the patient's upper jaw. The lower member includes a handle at one end and a downwardly facing surface at an opposite end configured for engaging posterior teeth (or the entire half-arch) of the patient's lower jaw. In a preferred form of the invention, the movable coupling is a pivotable, slidable, and releasable coupling. In another preferred form of the invention, the lower member includes a clamp for adjustably securing the patient's mandible to the lower member.

The invention further provides a method of using the device to distract a temporomandibular joint and reposition a dislocated disc in a patient. The method comprises the steps of positioning the device in the patient's mouth so that the distal tips of the elongated members are seated on upper and lower half-arches of the patient, squeezing the handles together to pivot the members and distract the joint, and sliding the lower member longitudinally relative to the upper member to reestablish the desired condyle-disc relationship. A repositioning splint may be placed in the patient's mouth after the device is removed to maintain the jaw in an open position while the disc heals.

This invention provides a device for distracting a temporomandibular joint in a patient suffering from intra-articular adhesions. The device comprises first and second elongated members configured for being coupled together at a first location and for providing a fulcrum at a second location. Each member includes a handle at one end and an opposite distal tip configured for engaging teeth of the upper or lower jaws. In a preferred form of the invention, the fulcrum is located intermediate the distal tips and the first location. In another preferred form of the invention, the fulcrum is adjustable and removable.

The invention further provides a method of using the device to distract a temporomandibular joint in a patient suffering from intra-articular adhesions. The method comprises the steps of coupling the first elongated member to the second elongated member at a first location, and providing a fulcrum at a second location. The method further comprises positioning the device in the patient's mouth so that the distal tips of the members are adjacent one another and seated on upper and lower teeth of the patent, and squeezing the handles together to cause the members to pivot about the fulcrum to distract the joint. In a preferred form of the invention, the fulcrum is adjustable and the method further comprises adjusting the height of the fulcrum.

These and other benefits and features of the invention will be apparent upon consideration of the following detailed description of preferred embodiments thereof, presented in connection with the following drawings in which like reference numerals identify like elements throughout.

BRIEF DESCRIPTION OF THE DRAWINGS

FIG. 3 is an enlarged, partial-side-sectional view of a central portion of the device of FIG. 1.

FIG. 4 is a front, cross-sectional view of the central portion of the device of FIG. 1 taken along line 4—4 in FIG. 3.

FIG. 5A is a schematic representation showing the device of FIG. 1 being positioned in the jaw of a patient suffering from a complete anterior dislocation of the disc.

DETAILED DESCRIPTION OF THE PREFERRED EMBODIMENTS

Figure 1:
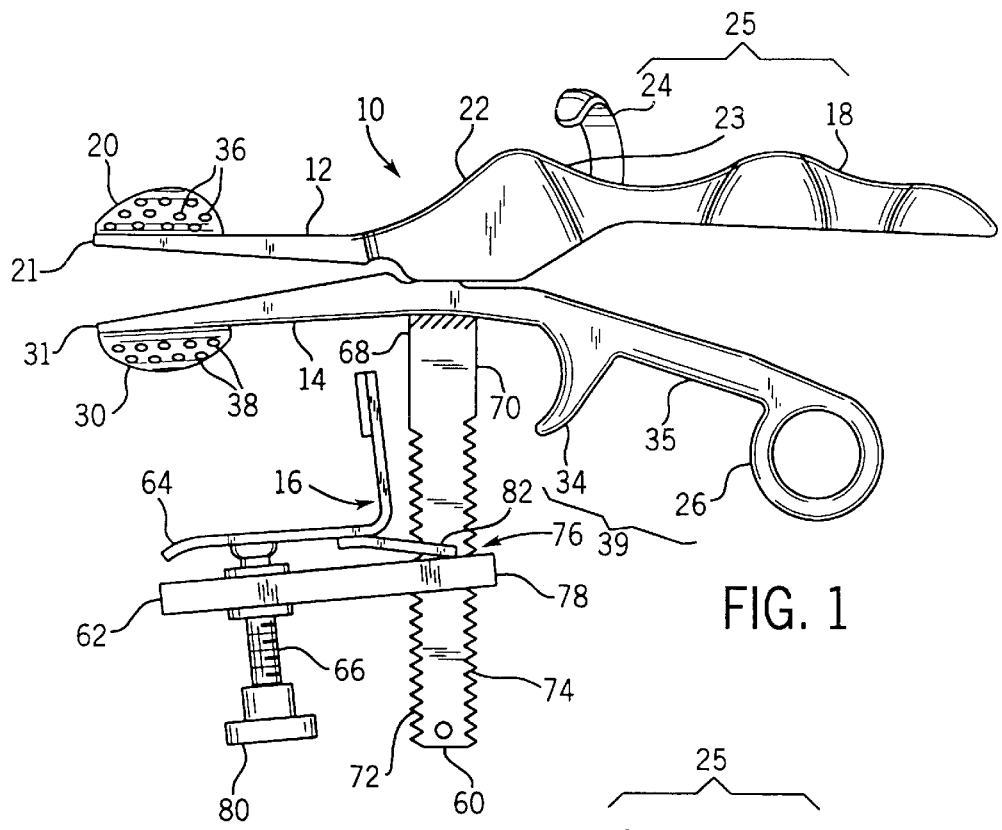
FIG. 1 is side elevation view of a device in accordance with the present invention.
Figure 2:
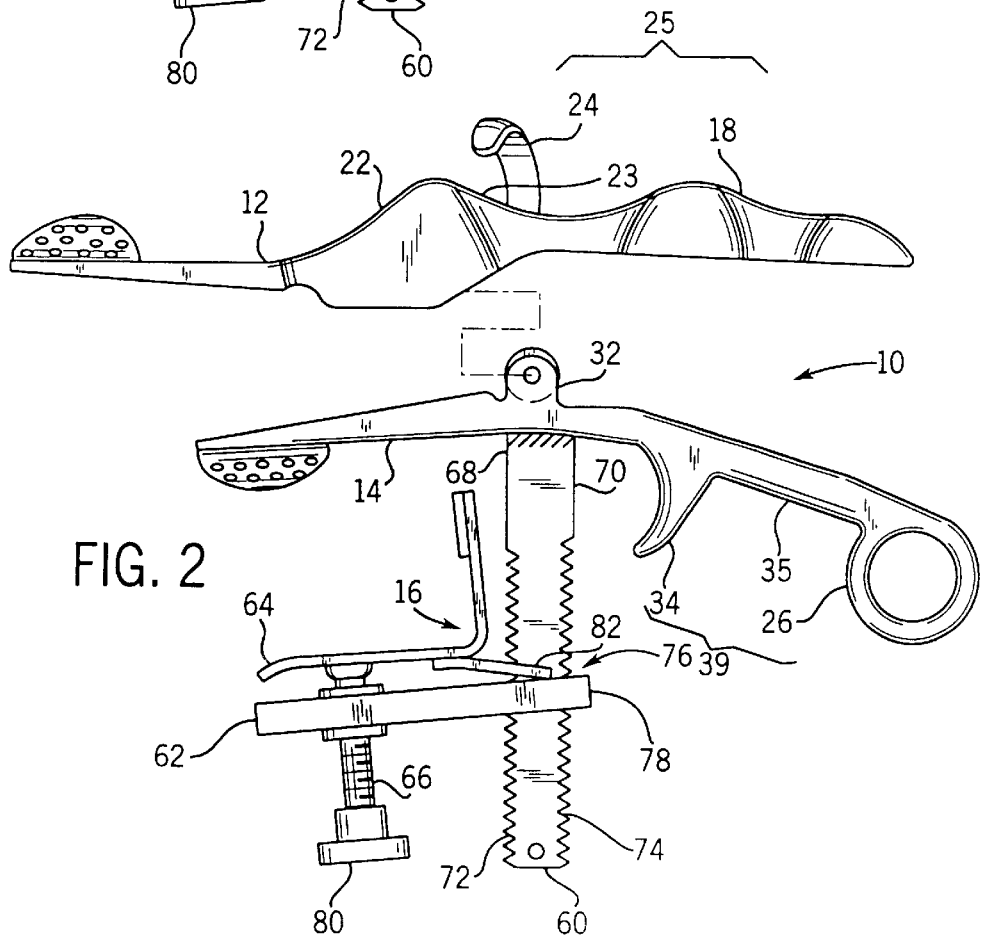
FIG. 2 is a partially exploded view of the device of FIG. 1.

As shown in FIGS. 1 and 2, a preferred embodiment of a device or instrument 10 used to facilitate the repositioning of an anteriorly dislocated disc in a temporomandibular joint of a patient comprises upper and lower elongated members 12, 14 and a mandibular (external) clamp 16. Upper member 12 includes a contoured palm grip 18 at one end, a receptacle 20 at an opposite distal tip 21, and a centrally located housing 22 and thumb catch 24. A surface 23 of housing 22 provides a convenient stop for the operator's thumb. Palm grip 18, thumb-stop 23 and thumb catch 24, taken together, define a handle 25 of upper member 12.

Lower member 14 includes a little-finger grip 26 at one end, a receptacle 30 at an opposite distal tip 31, and a centrally located roller 32 and forefinger rest 34. A tubular portion 35 of member 14 intermediate little-finger grip 26 and forefinger catch 34 provides an area that is grasped by the operator's middle and index fingers. Receptacles 20 and 30 face in opposite directions and are configured for engaging the upper and lower posterior teeth, respectively, of the patient. Preferably, receptacles 20, 30 include perforations 36, 38, respectively, the purpose of which is described below. Little-finger grip 26, tubular portion 35 and forefinger catch 34, taken together, define a handle 39 of lower member 14.

As best seen in FIGS. 3 and 4, upper member 12 is configured to releasibly, slidably and pivotally couple with lower member 14. This versatile coupling arrangement is accomplished by providing housing 22 of upper member 12 with a longitudinally extending cavity 40 configured to receive roller 32 of lower member 14. As best seen in FIG. 4, cavity 40 of upper member 12 is defined by a pair of vertical side walls 42, 44, a horizontal top wall 46, and a curved front wall 48. Thus, cavity 40 is preferably open to the bottom and the rear. Cavity 40 also includes a pair of opposed rails 50, 52 that extend longitudinally along respective side walls 42, 44 from curved front wall 48 to the open rear of cavity 40. Roller 32 of lower member 14 comprises a wheel 54 rotatably supported within an axle support 56 on an axle 58, which protrudes laterally from both exterior side surfaces of axle support 56. As best seen in FIG. 4, axle 58 and axle support 56 are configured such that the lateral protrusions of axle 58 slidably ride in opposed rails 50, 52 of cavity 40 whenever upper member 12 is coupled with lower member 14. As can also be seen, wheel 54 is configured to ride along top wall 46 of cavity 40 whenever members 12 and 14 are coupled together.

As will be evident to one of ordinary skill in the art, the foregoing coupling arrangement between the two members 12 and 14 permits relative pivoting movement about axle 58. In addition, the coupling arrangement permits the two member 12 and 14 to move longitudinally relative to one another with good lateral stability and smooth travel. Moreover, the coupling arrangement also permits the two members 12 and 14 to be easily separated from one another, which facilitates cleaning of instrument 10. Upper and lower members 12, 14 may be made of any suitable material known to those skilled in the art, such as stainless steel or a high density plastic.

Returning now to FIGS. 1 and 2, clamp 16 comprises a blade 60, a slide bar 62, a chin support 64, and an adjustable thumb screw 66. Preferably, blade 60 is fixedly attached (e.g., welded) to lower member 14 and extends generally perpendicularly thereto from a location directly beneath roller 32. Blade 60 includes front and rear edges 68, 70 which may be provided with teeth 72, 74, respectively. Slide bar 62 preferably includes a slot 76 that is long enough to allow bar 62 to be easily moved vertically along blade 60 whenever bar 62 is held in a substantially perpendicular orientation relative to blade 60, but short enough to cause the front and rear edges of slot 76 to engage teeth 72, 74 (and thereby lock bar 62 in place) whenever bar 62 is not substantially perpendicular to blade 60. In addition, slot 76 is preferably located close to an end 78 of bar 62 so that bar 62 automatically assumes a small angle relative to the perpendicular orientation (which thus locks bar 62 in place) due to the weight of bar 62 whenever the operator does not intentionally maintain the perpendicular orientation. Chin support 64 is attached to one end of thumb screw 66 above bar 62, and a knob 80 is attached to the other end of screw 66 below bar 62. Chin support 64 preferably includes a forked extension 82 that engages front edge 68 of blade 60 to maintain support 64 in a desired forward facing relationship when knob 80 and screw 66 are rotated.

As will be evident to one of ordinary skill in the art, the foregoing arrangement of clamp 16 permits bar 62 to be easily slid along blade 60 for making large (or rough) adjustments in the vertical separation between receptacle 30 and chin support 64. In addition, the arrangement permits small (or fine) adjustments in the vertical separation to be made by simply rotating knob 80 in the appropriate direction. Moreover, slide bar 62 can be easily separated from blade 60, which facilitates cleaning of instrument 10. Clamp 16 is preferably made of stainless steel, which also facilitate cleaning.

Now that instrument 10 has been sufficiently described, a method of using instrument 10 to distract a temporomandibular joint 102 and reposition a dislocated disc 104 in a patient 100 will now be described with particular reference to the schematic representations of FIGS. 5A–5D and FIG. 6. Although the method is illustrated below in association with an anteriorly dislocated disc, the method can be used equally well where the disc dislocation is antero-medial, anterolateral, medial or lateral; or where the disc is degenerated.

As illustrated in FIG. 5A, a condyle 106 of a mandible 108 rests in an articular fossa 110 of a temporal bone 111 such that its anterior-superior surface closely approximates (or even contacts) the posterior-inferior surface of an articular eminence 112. As also illustrated, instead of articular disc 104 being positioned in its normal resting position on the superior angle of the condyle 106, it is positioned on the inferior surface of eminence 112 anteriorly of its normal resting position, i.e., patient 100 has suffered a complete anterior dislocation of disc 104.

In a preferred method of using instrument 10 to reestablish a normal or improved condyle-disc relationship in patient 100, a pliable thermoplastic resin is softened and placed in receptacles 20, 30 of upper and lower members 12, 14. Instrument 10 is then placed in the patient's mouth on the affected side and a bite registration of upper and lower posterior teeth 116, 118 is established. As the patient bites down (see FIG. 5A), some of the resin will seep out through perforations 36, 38 in receptacles 20, 30. Instrument 10 is then removed from the mouth and the resin is "set" with cool water. The resin that flows through perforations 36, 38 during the bite registration procedure also hardens and ensures that the hardened bite registration will remain securely locked in place for the remainder of the procedure. One of ordinary skill in the art will know of several thermoplastic resin materials suitable for making a bite registration, but one such thermoplastic resin routinely used is KERR PRECISION COMPOUND®. KERR is the U.S. manufacturer of this readily available, green-colored material.

Figure 5B:
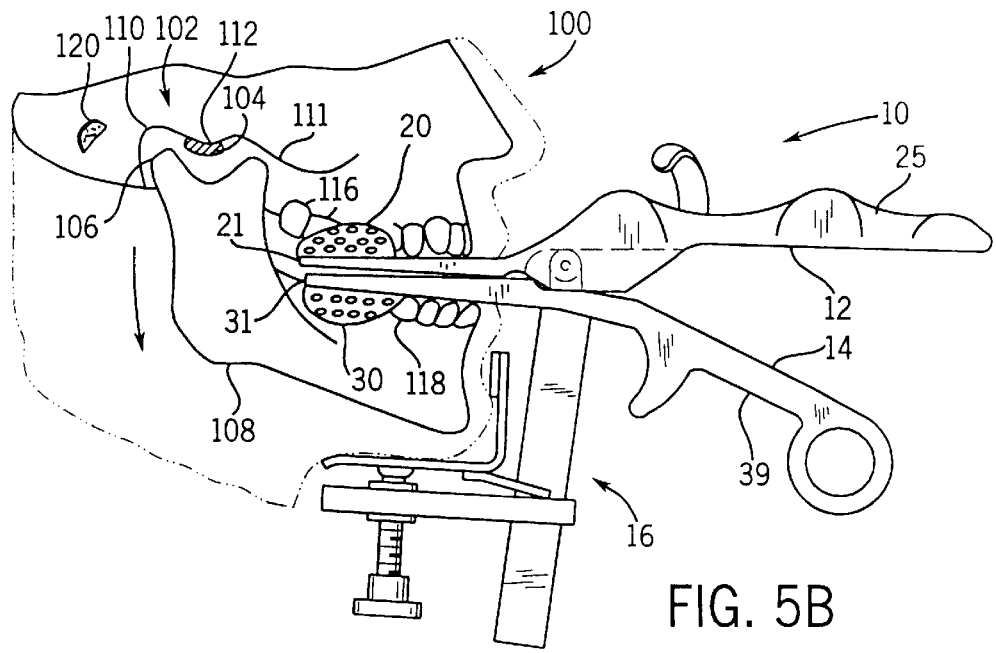
FIG. 5B is a schematic representation similar to FIG. 5A, but showing the device being used to distract the temporomandibular joint and lower the condyle from its normal resting position in the fossa.

Once the resin has been firmly set in receptacles 20, 30, instrument 10 is returned to the mouth and seated on the posterior teeth 116, 118 (or the half-arches) previously registered (see FIG. 5A). Mandibular clamp 16 is adjusted for contact with the patient's chin and adjacent lower border of the mandible. The operator's free hand (index and middle finger) is positioned just anterior to the external auditory meatus 120 on the affected side in order to palpate the movement of condyle 106 during the procedure. Handles 25, 39 of instrument 10 are squeezed together in one continuous motion to separate distal tips 21, 31 of upper and lower members 12, 14 and to thereby distract the temporomandibular joint. As can be seen, wheel 54 acts as a fulcrum point about which the upper and lower members 12, 14 pivot by pressing against top wall 46 of cavity 40. Once distal tips 21, 31 are sufficiently separated, handles 25, 39 are manipulated so that lower member 14 moves in an anterior direction (towards the front of the mouth) relative to upper member 12 (see FIGS. 5B and 5C).

Figure 5C:
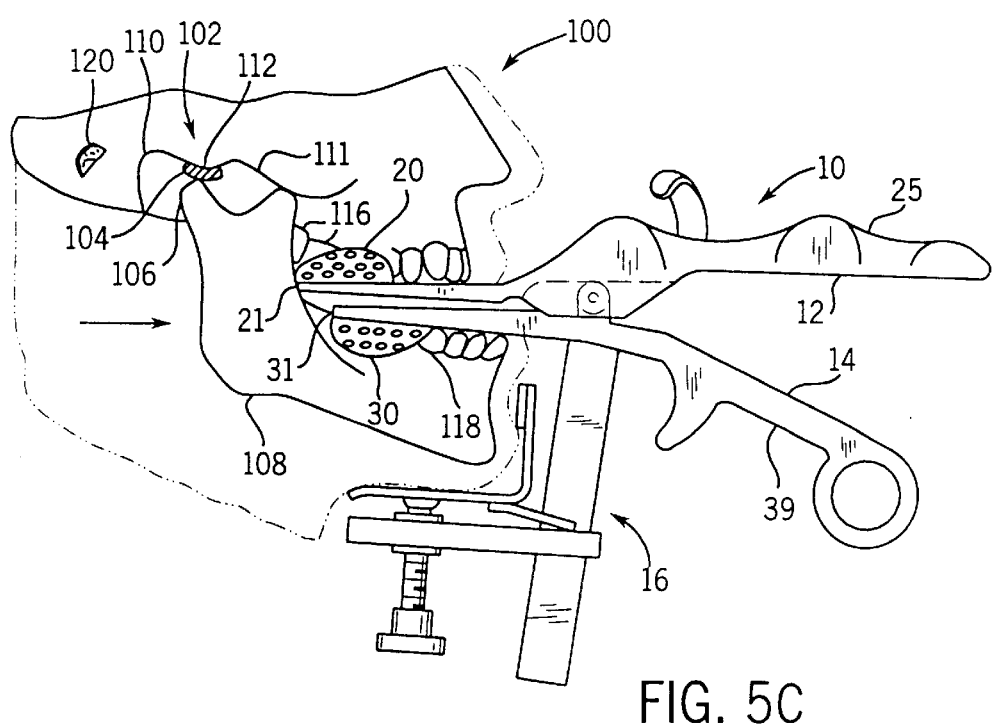
FIG. 5C is a schematic representation similar to FIG. 5B, but showing the device being used to maintain the temporomandibular joint in a distracted position while the mandible and condyle are translated anteriorly.
Figure 5D:
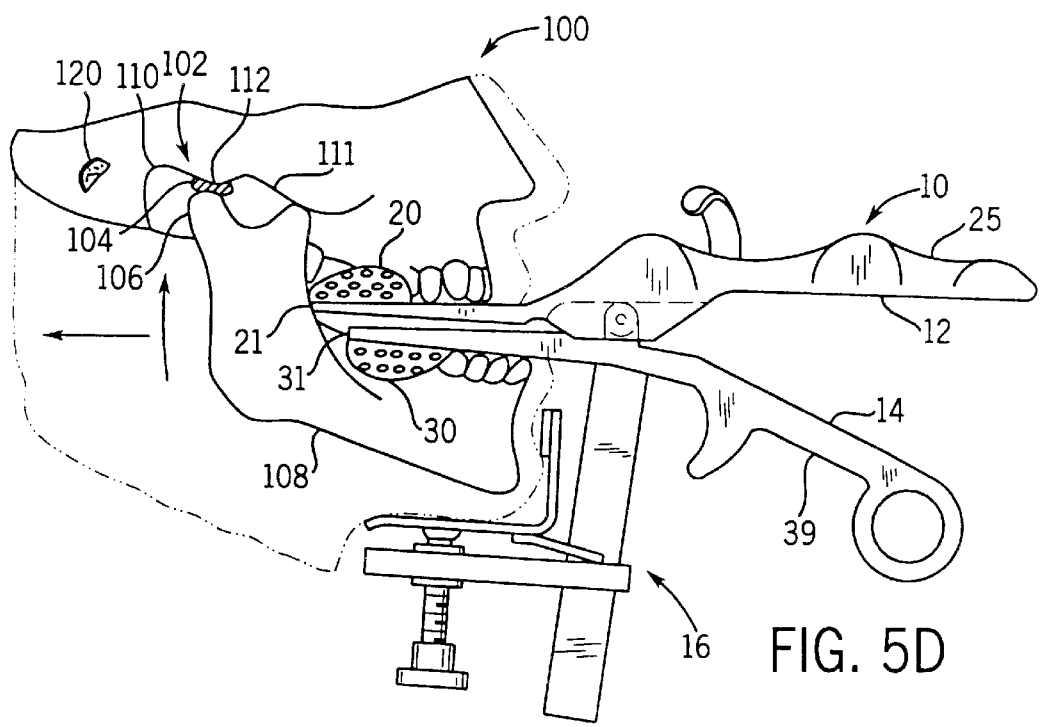
FIG. 5D is a schematic representation similar to FIG. 5C, but showing the device being used to reestablish a normal contact relationship between the condyle and the disc.
Figure 6:
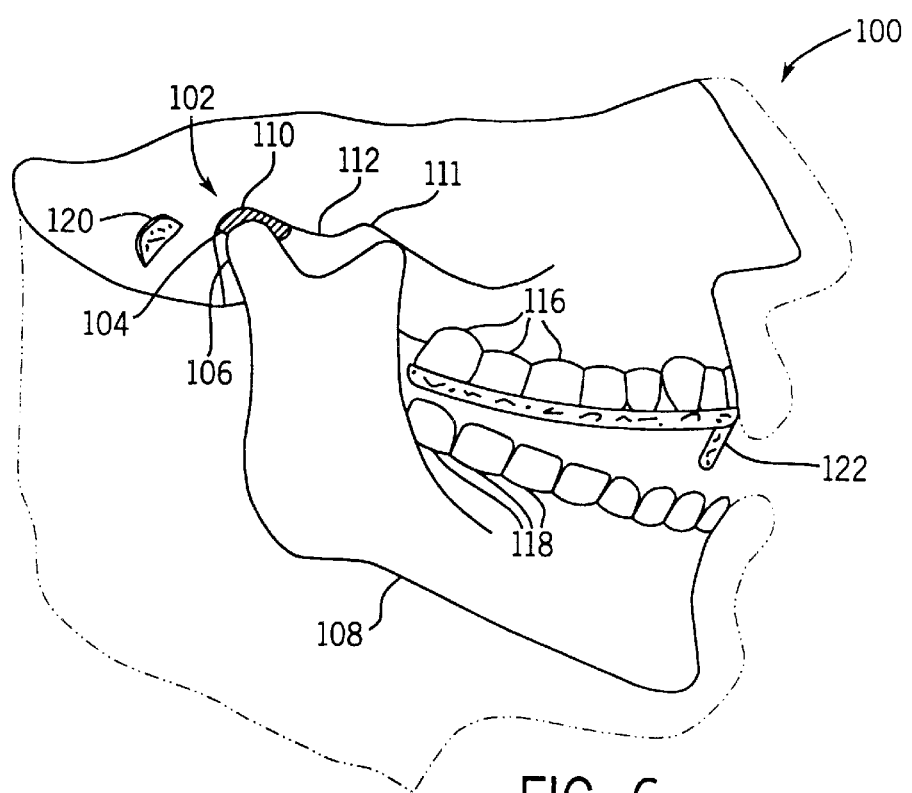
FIG. 6 is a schematic representation similar to FIG. 5D, but showing an anterior repositioning splint being used to maintain the jaw in an open position after the normal condyle-disc-fossa relationship has been reestablished with the device.

As will be evident to one of ordinary skill in the art, the net effect of the above-described action of instrument 10 is to move condyle 106 downward out of fossa 110 and forward onto anteriorly positioned disc 104 (see FIG. 5C). The procedure is concluded by releasing the pressure from handles 25, 39 (see FIG. 5D), loosening exterior clamp 16, and removing instrument 10 from the patient's mouth. Preferably, the mouth is then held open while an anterior repositioning splint 122 is immediately placed in the patient's mouth to ensure that the reestablished condyle-disc relationship is maintained until the disc heals (see FIG. 6). Splint 122 is an orthodontic device that is well known to those of ordinary skill in the art.

Referring now to FIGS. 7–12, another embodiment of a device or instrument 10' useful for distracting a temporomandibular joint and/or repositioning an anteriorily dislocated disc in a patient will now be described. For brevity, the written description of device 10' that follows will generally be limited to aspects thereof which differ from device 10 described above. The components in device 10' that are similar in structure and function to like-components in device 10 (described above in connection with FIGS. 1–6) will be designated by the same reference numerals but with a prime designation.

Figure 7:
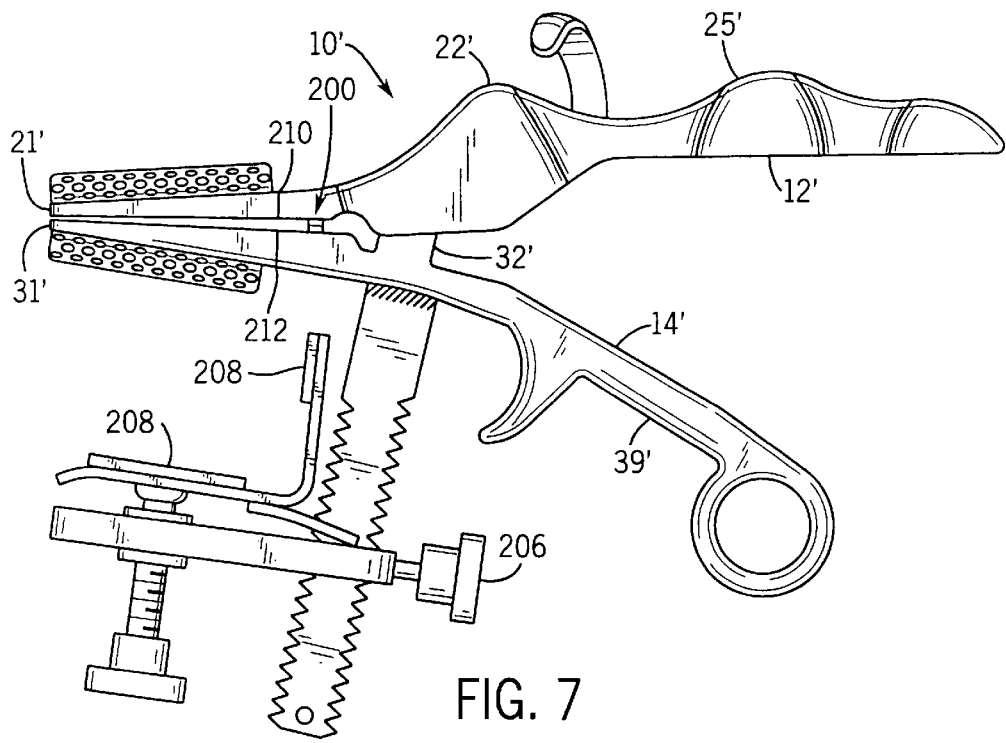
FIG. 7 is side elevation view of a device in accordance with a second embodiment of present invention.
Figure 8:
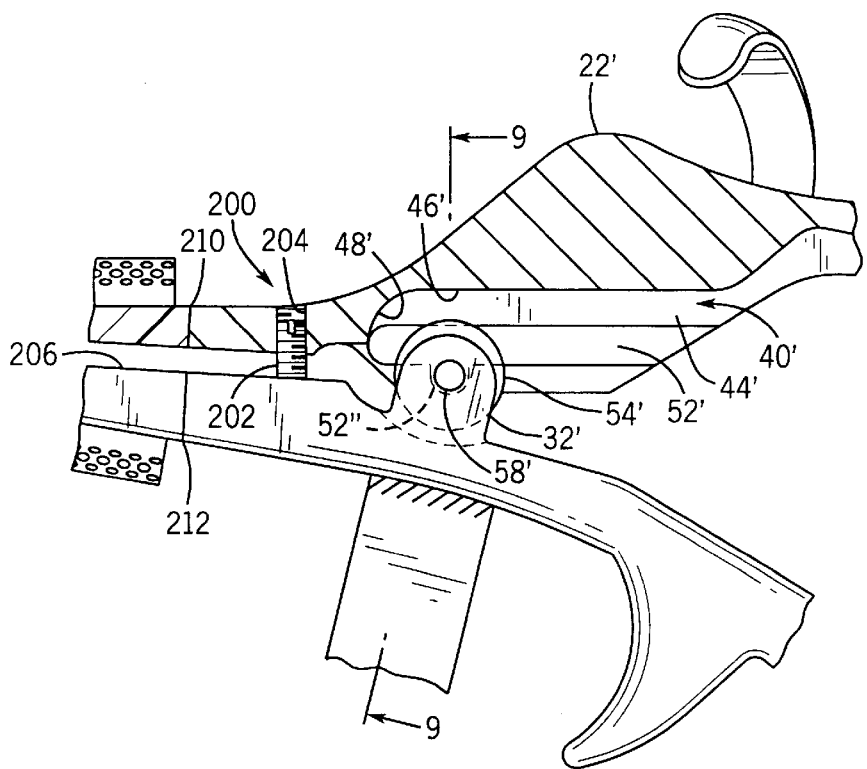
FIG. 8 is an enlarged, partial-side-sectional view of a central portion of the device of FIG. 7.
Figure 10:
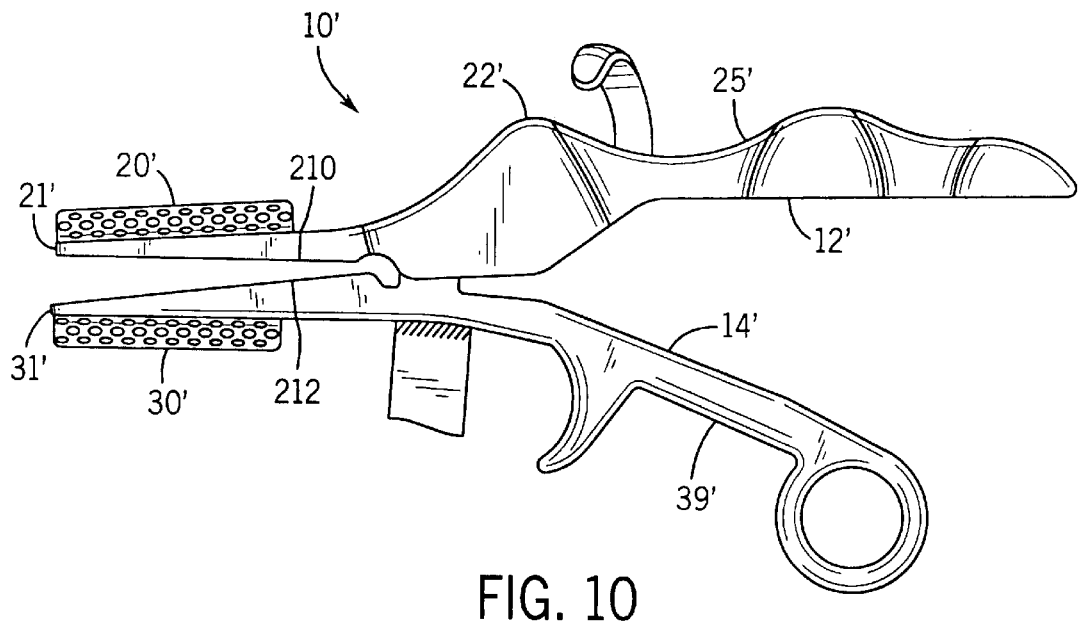
FIG. 10 is side elevation view of the second embodiment of FIG. 7, but showing the elongated members of the device pivoting about a fulcrum located in front of the coupling between the members.
Figure 11:
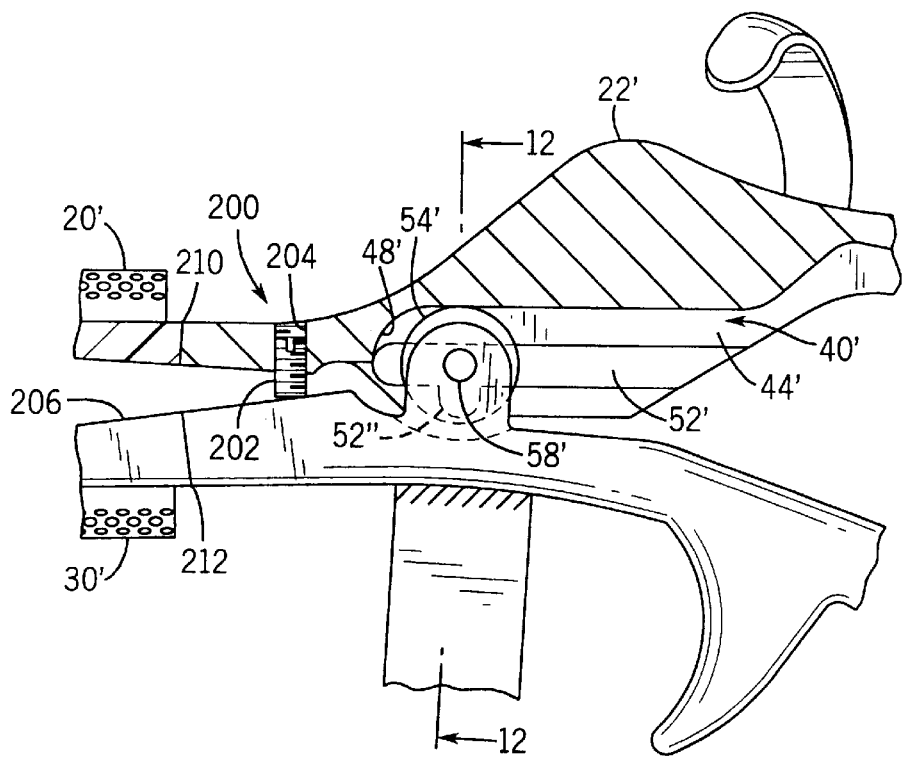
FIG. 11 is an enlarged, partial-side-sectional view of a central portion of the device of FIG. 10.
Figure 9:
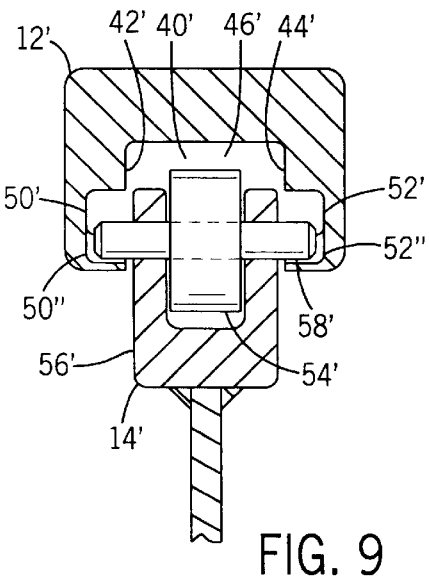
FIG. 9 is a front, cross-sectional view of the central portion of the device of FIG. 7 taken along line 9—9 in FIG. 8.
Figure 12:
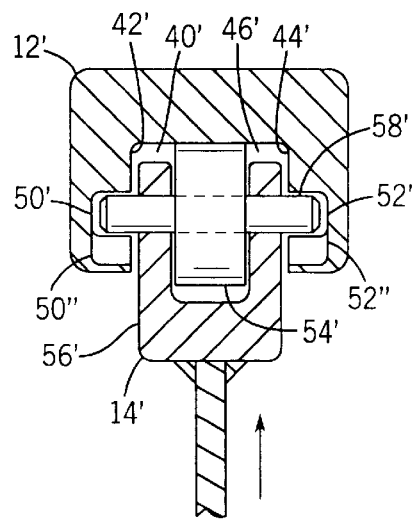
FIG. 12 is a front, cross-sectional view of the central portion of the device of FIG. 10 taken along line 12—12 in FIG. 11.

Device 10' is similar to device 10 described above in that the upper and lower members 12', 14' are coupled together by an arrangement that allows for pivoting and sliding relative movement between the members. In addition, the coupling allows for upper and lower members 12', 14' to be easily uncoupled when desired, such as for cleaning purposes. In FIGS. 7–9, device 10' is shown with the upper and lower members 12' and '14 pivoted such that distal tips 21', 31' engage each other (hereinafter referred to as the "closed" orientation). In FIGS. 10–12, device 10' is shown with the upper and lower members 12' and 14' pivoted such that distal tips 21', 31' are separated from each other (hereinafter referred to as the "open" orientation).

As can be seen, upper and lower members 12' and 14' are similar in most respects to upper and lower members 12 and 14 of device 10 described above. In particular, upper member 12' of device 10' includes a housing 22' provided with a longitudinally extending cavity 40' configured to receive a roller 32' of lower member 14' (see FIG. 8). Cavity 40' is defined by a pair of opposed side walls 42', 44', a top wall 46', and a curved front wall 48' (see FIGS. 8–9). Cavity 40' includes a pair of opposed rails 50', 52' extending longitudinally along respective side walls 42', 44' from a curved front wall 48' to an open rear of cavity 40'. Roller 32' of lower member 14' includes a wheel 54' rotatably supported on an axle 58' that protrudes laterally from the two exterior side surfaces of an axle support 56'. The two opposed lateral protrusions of axle 58' are configured to slidably ride in opposed rails 50', 52' of cavity 40' to provide the coupling with releasable, slidable and pivotable movement.

Device 10' differs from the previously described device 10 in a number of significant respects. One such difference is that device 10' includes an enhanced power configuration. This enhanced power configuration is made possible by constructing upper member 12' with an auxiliary fulcrum 200 that provides a more advantageous pivot lever between upper and lower members 12' and 14' than exists between upper and lower members 12 and 14 of device 10. That is, while devices 10 and 10' both include a fulcrum defined by the wheel 54' (or 54) pressing against the associated top wall 46' (or 46), device 10' also includes auxiliary fulcrum 200 located at a position forward of wheel 54'. As illustrated, fulcrum 200 is constructed in upper member 12' at a position between curved front wall 48' and distal tip 21'. Fulcrum 200 may be adjustable in height to provide a fulcrum of the desired size at a location forward of wheel 54', or completely retracted into upper member 12' (or simply removed) so that wheel 54' serves as the fulcrum in the manner discussed above in connection with device 10. As illustrated, fulcrum 200 comprises a screw 202 that is threadedly received within a bore hole 204 formed in upper member 12'. Fulcrum 200 could instead be formed in lower member 14', or in a combination of the upper and lower members 12', 14'. Moreover, fulcrum 200 could be constructed so as to be adjustable in location along the longitudinal axes of the elongated members 12', 14' to further increase or decrease the strength of the leverage provided by the fulcrum.

When fulcrum 200 is used as the pivot point, it is necessary to provide cavity 40' of device 10' with a pair of auxiliary rails 50", 52" that intersect with respective main rails 50', 52'. As best illustrated in FIGS. 8–9, opposed auxiliary rails 50", 52" extend perpendicular relative to main rails 50', 52' and are configured to receive the opposed lateral protrusions of axle 58'. This arrangement of main rails 50', 52' intersecting auxiliary rails 50", 52" allows roller 32' to move horizontally within housing 22' along opposed main rails 50', 52' as well as vertically within housing 22' along opposed auxiliary rails 50", 52".

Now that the enhanced power configuration of device 10' has been described, a preferred method of using device 10' in this configuration to unlock the jaw of a patient suffering temporomandibular joint locking will now be set forth. The enhanced power configuration will be particularly useful when the patient's jaw suffers from intra-articular adhesions, in which case the arrangement of device 10 (where the fulcrum is located at the wheel) may not provide enough leverage to break the adhesions. The enhanced power configuration provides increased leverage because the fulcrum is repositioned from the location of wheel 54' to a location closer to the distal tips of device 10'. The device 10' can be placed in this power configuration by bringing distal tips 21', 31' together (see FIG. 7)—which causes axle 58' to align with the auxiliary rails 50", 52"—and then tightening screw 204 until it contacts an upper surface 206 of lower member 14' (see FIG. 8). As screw 204 is tightened (and the fulcrum is increased in height), the lateral projections of axle 58' will move vertically along opposed auxiliary rails 50", 52" so long as the device 10' is maintained in the closed orientation (see FIG. 9). Once the fulcrum 200 has reached the desired height, the device 10' is ready to be used in the enhanced power configuration.

To use the device 10' in the enhanced power configuration, the operator inserts it into the patient's mouth in the same way as described above for device 10 (see FIG. 5A). Upon squeezing handles 25', 39' together, roller 32' will move upwardly in cavity 40' as the lateral projections of axle 58' move upwardly along vertical rails 50", 52" (see FIGS. 10–12). As will be appreciated by those skilled in the art, having the fulcrum at a location closer towards distal tips 21', 31' than the wheel location of device 10 provides a more advantageous lever. Hence, less effort is required by the operator to free the jaw from the adhesions and/or to distract the temporomandibular joint.

If the patient is also suffering from a dislocated disc, screw 204 can be easily retracted back into hole 202 to once again relocate the fulcrum at the location of wheel 54'. Once this is done, device 10' can be used as described above in the method for using device 10 to reposition the dislocated disc and obtain the proper condyle-disc relationship.

Now that the enhanced power configuration of device 10' has been described, some additional enhancements contemplated for devices 10 and 10' will be described. Although these enhancements are described and illustrated below in the context of device 10', they are equally applicable to device 10 or any other similar devices or embodiments within the scope of the claims that follow.

FIG. 7 illustrates an enhancement to the mandibular (external) clamp 16' of device 10'. As can be seen, clamp 16' differs from clamp 16 of device 10 in that it includes an adjustable thumb screw 206 for more securely locking the slide bar 62' to the blade 60' at any desired location. In addition, the chin support 64 may be provided with cushions or pads 208 made of any suitably soft and/or elastomeric material for enhancing the comfort of the patient.

Figure 13:
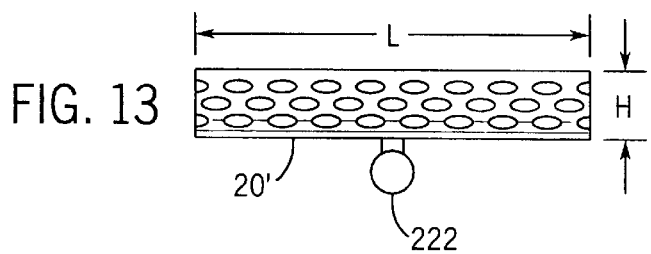
FIG. 13 is a side elevation view of the receptacle portion of the device of FIG. 10.
Figure 14:
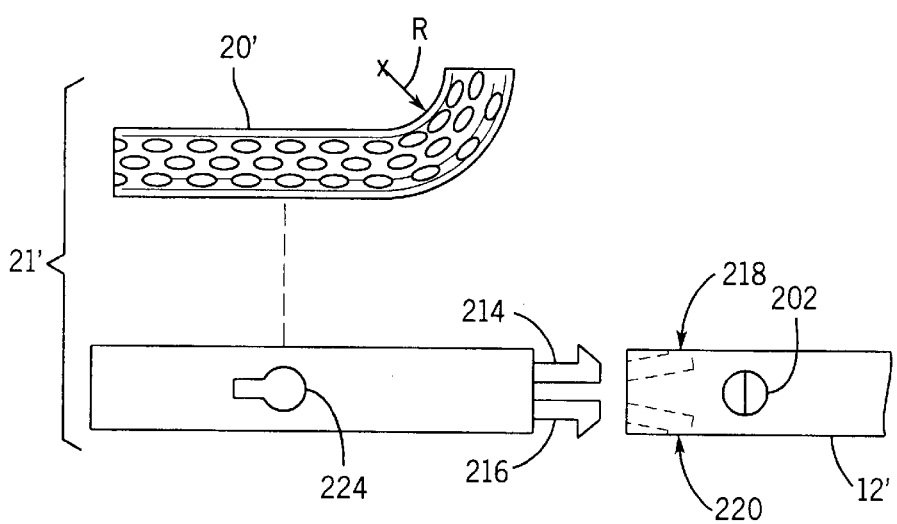
FIG. 14 is an exploded top profile view of the receptacle and distal tip portion of the device of FIG. 10.

FIGS. 7–14 also illustrate various enhancements for increasing the adaptability of the device to patients of different sizes and anatomies (e.g., adult, teen and children sizes). According to one such enhancement, distal tips 21' and 31' are constructed so that they are easily removed from a base portion of upper and lower members 12' and 14' at junction points 210 and 212 (see FIGS. 8, 11 and 14). One possible structure for releasably joining distal tip 21' to the base portion of upper member 12' to form the complete upper member 12' is illustrated in FIG. 14. In the illustrated coupling, a pair of flexible barbs 214, 216 are formed on distal tip 21' and configured to extend into a pair of bent passageways 218, 220 formed in the base portion of upper member 12'. Those skilled in the art will recognize that numerous other structures may be used for releasably securing distal tip 21 to the base portion of the upper member 12', such as a threaded bolt (not shown) projecting from distal tip 21' and extending into a mating bore (not shown) formed in upper member 12'. Distal tips 21' and 31' can be made from any suitable material including metal such as stainless steel, but in FIGS. 8 and 11 they are illustrated as being made from a plastic material that has the necessary rigidity and strength but is less costly from a manufacturing standpoint. In this way, the device is less expensive to manufacture, and the distal tips can be disposed after each use without undue expense.

Another enhancement to device 10' that improves its adaptability to different size patients and anatomies, and also improves its ease of use, involves constructing the receptacles 20' and 30' so that they are removable from the distal tips 21' and 31'. One possible structure for releasably joining receptacles 20' to distal tip 21' is illustrated in FIGS. 13 and 14. In the illustrated coupling, the lower surface of receptacle 21' includes a downwardly depending post and ball structure 222, which is configured to engage a complementary slot 224 formed in the distal tip 21'. Those skilled in the art will recognize that numerous other coupling structures can be used for releasably securing receptacle 20' to distal tip 21', such as a small screw (not shown) projecting from receptacle 20' (or from distal tip 21'). Receptacles 20' and 30' can be made from any suitable material including a metal such as stainless steel, but in the illustration they are made from a plastic material that provides the necessary rigidity and strength. By having removable receptacles, patients having different arch sizes and anatomies are more easily accommodated. For example, for a smaller patient it would typically be desirable to use receptacles having a shorter height "H" (see FIG. 13) and a shorter length "L" than would be used for a larger patient.

The ability to utilize customizable/replaceable receptacles 20', 30' and/or distal tips 21', 31' results in other advantages. For example, the technician is able to select receptacles that are of the appropriate length and curvature (or radius) "R" (see FIG. 14) so that they can engage not only the posterior teeth of the upper and lower jaws (as described above in connection with device 10) but also the canine teeth and even the incisor teeth. That is, the upper and lower receptacles can be configured to engage the entire upper and lower half-arches of the patient. By having the receptacles 20' and 30' of the device 10' engage not only the upper and lower posterior teeth, but the entirety of the upper and lower half-arches, the comfort of the patient is increased and the device is more easily seated in the patient's mouth by the technician. Of course, when receptacles 20' and 30' of the device 10' are configured to engage all the teeth of the upper and lower quadrants, it will be necessary to have separate left and right receptacles in all the common sizes.

Another advantage of having replaceable receptacles 20', 30' and/or distal tips 21', 31' is that they can be manufactured with impression material premolded into the receptacle portion. Those skilled in the art will recognize that a wide variety of impression materials can be used, including numerous well known resins or elastomer materials that have the desired resiliency and toughness and setting properties. One material that is particularly suitable for use in the present invention is ELVAX®, manufactured by the DU PONT Company. By having the receptacles 20' and 30' pre-filled with this or another suitable impression material, the use of the device is further simplified because the technician need not bother with the step of filling the receptacles. Moreover, the procedure is also simplified in that the receptacle and/or distal tip can simply be discarded after the procedure is complete, thus eliminating some of the clean-up steps.

Numerous characteristics, advantages, and embodiments of the invention have been described in detail in the foregoing description with reference to the accompanying drawings. However, the disclosure is illustrative only and the invention is not limited to the precise illustrated and described embodiments. Various changes and modifications may be effected by one skilled in the art without departing from the scope or spirit of the present invention. Thus, the scope of the invention is limited only by the claims which follow.

What is claimed is:

1. A method of using a device to distract the temporomandibular joint of a patient, the device including first and second elongated members coupled together at a first location, the first member having a first handle at one end and a first distal tip at an opposite end, and the second member having a second handle at one end and a second distal tip at an opposite end, the method comprising:

positioning the device in the mouth of the patient so that the first distal tip engages teeth in the upper jaw and the second distal tip engages teeth in the lower jaw; and squeezing the first and second handles together to separate the first and second distal tips and thereby distract the temporomandibular joint.

2. The method of claim 1, wherein the first and second members are slidably coupled together at the first location, the method further comprising:

after squeezing the handles together, sliding the second handle in a longitudinal direction relative to the first handle.

3. The method of claim 1, further comprising:

after squeezing the handles together, removing the device from the mouth of the patient; and inserting a repositioning splint in the mouth to maintain the lower jaw in a desired position.

4. The method of claim 1, wherein the first and second members are releasibly coupled together, the method further comprising:

before positioning the device, joining the first and second members together.

5. The method of claim 1, wherein the second member includes a mandibular clamp, the method further comprising:

before squeezing the handles together, adjusting the clamp to secure the mandible of the patient to the second member.

6. The method of claim 5, wherein the clamp comprises a blade extending generally perpendicularly from the second member and a chin support configured to slide along the blade, and wherein the step of adjusting the clamp comprises:

sliding the chin support along the blade to adjust a vertical separation between the chin support and a lower surface of the second member.

7. The method of claim 5, wherein the clamp comprises a chin support mounted on a threaded member, and wherein the step of adjusting the clamp includes:

rotating the threaded member to adjust a vertical separation between the chin support and a lower surface of the second member.

8. The method of claim 1, further comprising, before squeezing the handles, establishing bite registrations between the first distal tip and the upper teeth and between the second distal tip and the lower teeth.

9. The method of claim 1, wherein the first distal tip includes a first upwardly facing receptacle and the second distal tip includes a second downwardly facing receptacle, and wherein the step of establishing the bite registrations includes:

inserting the receptacles in the mouth and having the patient temporarily bite down upon an impression material in the first and second receptacles;

removing the device from the mouth of the patient; and setting the impression material to fix the teeth impression.

10. The method of claim 9, further comprising, before inserting the device in the mouth of the patient, filling the first and second receptacles with the impression material.

11. The method of claim 9, further comprising, before inserting the device in the mouth of the patient, selecting the first and second receptacles that are pre-filled with the impression material.

12. The method of claim 1, wherein the first and second distal tips include first and second receptacles that are detachable, the method further comprising:

selecting the first and second receptacles so that they are of the appropriate size and configuration for the age and anatomy of the patient; and joining the first and second receptacles to the first and second distal tips.

13. The method of claim 1, wherein each of the first and second distal tips is detachable from a base portion of the first and second members, the method further comprising:

selecting the first and second distal tips so that they are of the appropriate size and configuration for the age and anatomy of the patient; and joining the first and second distal tips to the base portions of the first and second members.

14. The method of claim 1, further comprising, before squeezing the handles together, providing an auxiliary fulcrum intermediate the first location and the distal tips, the auxiliary fulcrum being of sufficient height so that the first and second members pivot about the auxiliary fulcrum when the first and second handles are squeezed together.

15. The method of claim 14, wherein the auxiliary fulcrum is adjustable in height, further comprising the step of adjusting the height of the fulcrum prior to squeezing the first and second handles together.

16. The method of claim 15, wherein the auxiliary fulcrum is provided by a screw, and wherein the step of adjusting the height of the fulcrum comprises rotating the screw.

17. The method of claim 1, wherein the first and second members are pivotally coupled together, and wherein the step of squeezing the first and second handles together causes the members to pivot about a wheel located at the first location.

18. The method of claim 1, wherein the first and second distal tips are configured to engage the upper and lower half-arches on one side of the upper and lower jaws.

19. The method of claim 1, wherein the first and second distal tips are configured to engage at least the posterior teeth on one side of the upper and lower jaws.

20. A method of using a device to reposition a dislocated disc in a temporomandibular joint of a patient, the device including elongated upper and lower members pivotally and slidably coupled together, each member having a handle at one end and a teeth-engaging surface at an opposite, the method comprising:

positioning the device in the mouth of the patient so that the teeth-engaging surface of the upper member engages teeth of the upper jaw and the teeth-engaging surface of the lower member engages teeth of the lower jaw;

squeezing the handles together to separate the upper and lower jaws and distract the joint;

sliding the lower member in an anterior direction relative to the upper member; and releasing the handles to establish a normal condyle-disc relationship.

21. The method of claim 20, wherein the teeth-engaging surfaces of the upper and lower members are configured to engage the upper and lower half-arches on one side of the upper and lower jaws.

22. A device for distracting the temporomandibular joint of a patient, comprising:

an elongated first member having a first handle at one end and a first distal tip at an opposite end;

an elongated second member having a second handle at one end and a second distal tip at an opposite end, the second member being movably coupled to the first member at a first location; and a fulcrum at a second location, the fulcrum being configured to cause the first and second distal tips to separate when the first and second handles are squeezed together, the fulcrum being adjustable to increase or decrease a strength of leverage provided by the fulcrum.

23. The device of claim 22, wherein the fulcrum at the second location is intermediate the distal tips and the first location.

24. The device of claim 22, wherein the first location is a wheel-fulcrum and the second location is a screw-fulcrum located intermediate the distal tips and the first location.

25. The device of claim 22, wherein the fulcrum is adjustable in height.

26. The device of claim 22, wherein the fulcrum comprises a screw threaded into a bore formed in one of the members.

27. The device of claim 22, wherein the fulcrum comprises a wheel formed on one of the members which engages a longitudinally extending wall formed in the other of the members.

28. The device of claim 22, wherein the fulcrum is adjustable in position along the lengths of the elongated members.

29. The device of claim 22, wherein each of the distal tips is detachable from a base portion of the first and second members.

30. The device of claim 22, wherein the first and second distal tips include receptacles for holding an impression material.

31. The device of claim 30, wherein the receptacles are detachable.

32. The device of claim 22, wherein the first and second members are movably coupled together by a pair of posts formed on the first member, the posts being slidably received in opposed channels formed in the second member.

33. The device of claim 32, wherein the opposed channels include a first pair of opposed channels extending lengthwise along the second member and a second pair of opposed channels extending perpendicular to and intersecting with the first pair of opposed channels.

* * * * *